(12) United States Patent
Bhatnagar et al.

(10) Patent No.: US 7,727,782 B2
(45) Date of Patent: Jun. 1, 2010

(54) APPARATUS FOR IMPROVING INCOMING AND OUTGOING WAFER INSPECTION PRODUCTIVITY IN A WAFER RECLAIM FACTORY

(75) Inventors: Yashraj K. Bhatnagar, Santa Clara, CA (US); Krishna Vepa, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 179 days.

(21) Appl. No.: 11/823,061

(22) Filed: Jun. 25, 2007

(65) Prior Publication Data

US 2008/0318350 A1    Dec. 25, 2008

(51) Int. Cl.
*H01L 21/66* (2006.01)
(52) U.S. Cl. ........................................................ 438/16
(58) Field of Classification Search ........................ None
See application file for complete search history.

(56) References Cited

U.S. PATENT DOCUMENTS

| | | | |
|---|---|---|---|
| 5,849,099 A | 12/1998 | McGuire | |
| 5,981,301 A | 11/1999 | Muramatsu et al. | |
| 6,406,923 B1 | 6/2002 | Inoue et al. | |
| 6,458,712 B2 | 10/2002 | Kramer et al. | |
| 6,685,542 B2 | 2/2004 | Mori et al. | |
| 7,100,826 B1 | 9/2006 | Phan et al. | |
| 7,261,617 B1 | 8/2007 | Kim et al. | |
| 2002/0058418 A1 | 5/2002 | Lewis | |
| 2002/0081954 A1 | 6/2002 | Mori et al. | |
| 2006/0169900 A1* | 8/2006 | Noji et al. | 250/310 |
| 2006/0211218 A1 | 9/2006 | Boyle et al. | |
| 2007/0020784 A1* | 1/2007 | Timans | 438/16 |
| 2007/0203041 A1 | 8/2007 | Lee | |
| 2007/0228524 A1 | 10/2007 | Hayashida et al. | |

* cited by examiner

*Primary Examiner*—Charles D Garber
*Assistant Examiner*—Andre' C Stevenson
(74) *Attorney, Agent, or Firm*—Blakely, Sokoloff, Taylor & Zafman LLP

(57) ABSTRACT

An apparatus and method for inspecting wafers at a reclaim factory is described. Embodiments of the invention describe an apparatus in which a wafer ID and wafer thickness may be simultaneously measured. A wafer is placed onto a sloped surface and positioned by aligning a notch in the wafer with a pin located on the surface, and by propping the wafer against a pair of laterally opposite restraints. In one embodiment, a foot-switch is used to trigger the simultaneous wafer ID and wafer thickness measurements.

17 Claims, 7 Drawing Sheets

APPARATUS FOR IMPROVING INCOMING AND OUTGOING WAFER INSPECTION PRODUCTIVITY IN A WAFER RECLAIM FACTORY

BACKGROUND OF THE INVENTION

1. Field of the Invention

The present invention relates to the field of reclamation and reuse of semiconductor material substrates. More particularly this invention relates to an apparatus and method for inspecting incoming and outgoing wafers at a reclaim factory.

2. Discussion of Related Art

The increasing process complexity and introduction of new materials to the field of integrated circuit (IC) fabrication has given rise to a greater number of processing steps; each of which must be tested for quality.

Test wafers including "dummy" or "control monitor" wafers are used to check the reliability of IC fabrication equipment. For example, dummy wafers are used to test new IC fabrication equipment prior to its implementation into the large-scale production process of ICs. A dummy wafer is cycled through the new equipment and the ICs formed on the dummy wafer are then examined to determine if they meet certain specified criteria indicating that the fabrication process was properly performed. Only then is the equipment implemented into the production of ICs. Thereafter, the dummy wafer may be discarded, or "recycled" by removing the depositing films and re-using the dummy wafer.

Once fabrication equipment is implemented into the production process, it must be periodically inspected by examining the fabricated ICs to ensure that it is functioning properly. Such quality assurance testing is typically performed on a daily basis, such as at the beginning of every working shift. During such testing, control monitor wafers are used in a trial process, such as film deposition, performed on the wafer. The control wafer is then examined to determine if it meets certain specified criteria indicating that the fabrication process was properly performed. Thereafter, the control wafer maybe discarded (to protect intellectual property, for example), or "recycled" by removing the depositing films and re-using the control wafer.

All of this quality assurance testing requires the use of a large number of wafers and increases the total cost of IC fabrication. Customers will typically recycle their wafers using their own equipment. However, each recycle roughens the wafer surface and after a few such cycles the wafers must be re-polished to meet fab specifications for such wafers to be used in their tools. These wafers are typically sent to a wafer reclaim vendor who provides the essential expertise and service for stripping and re-polishing the wafers to the customer's specifications and returning them to the customer for a service charge. In addition to meeting customer specifications, the wafer reclaim vendor must ensure than one customer's wafers do not become mixed with another customer's wafers. The method typically employed to accomplish this is to record each wafer's identification (ID) code at the incoming stage and then tracking that wafer through the entire process.

The reclamation cycle forms a loop in which used wafers are sent to a reclaim vendor, processed to meet fab specification, and sent back to the customer for reuse as test wafers. Customers optimize cost-cutting by reducing the number of test wafers to be used, and by using them as many times as possible. This requires maintaining a high ratio of reclaimed wafers to total test wafers. In order to meet customer demands, wafer reclaim factories must in turn optimize the wafer reclaim process and offer cycle times in the order of days rather than weeks.

A typical wafer reclamation process includes multiple preliminary steps of incoming wafer inspection, ID detection, and sorting of the wafers into groups. The grouped wafers are then subjected to removal steps such as grinding and/or etching particular materials, followed by polishing and cleaning. The process is finalized with a final multi-step outgoing wafer inspection to ensure that the proper amount of material was removed, and that customer specifications such as those for surface particles and wafer flatness are met. A lot of attention has been given to optimization of the critical removal steps where proprietary grinding and etching steps are typically performed. However, what is additionally needed is a way to reduce overall cycle times at the incoming and outgoing wafer inspection steps.

SUMMARY OF THE INVENTION

An apparatus and method is disclosed for inspecting either incoming or outgoing wafers in a wafer reclaim factory. A wafer can be placed on a contact plate and aligned in the x-y axis parallel to the contact plate utilizing a wafer notch pin and a pair of restraints located on laterally opposite sides of the pin. The wafer ID, wafer thickness, film refractive index, and/or film x-ray fluorescence may then be simultaneously measured. In one embodiment, the contact plate is aligned at approximately a 15 degree angle to horizontal. In another embodiment, the wafer measurements can be triggered utilizing a foot-switch.

DETAILED DESCRIPTION OF THE PRESENT INVENTION

Figure 1A:
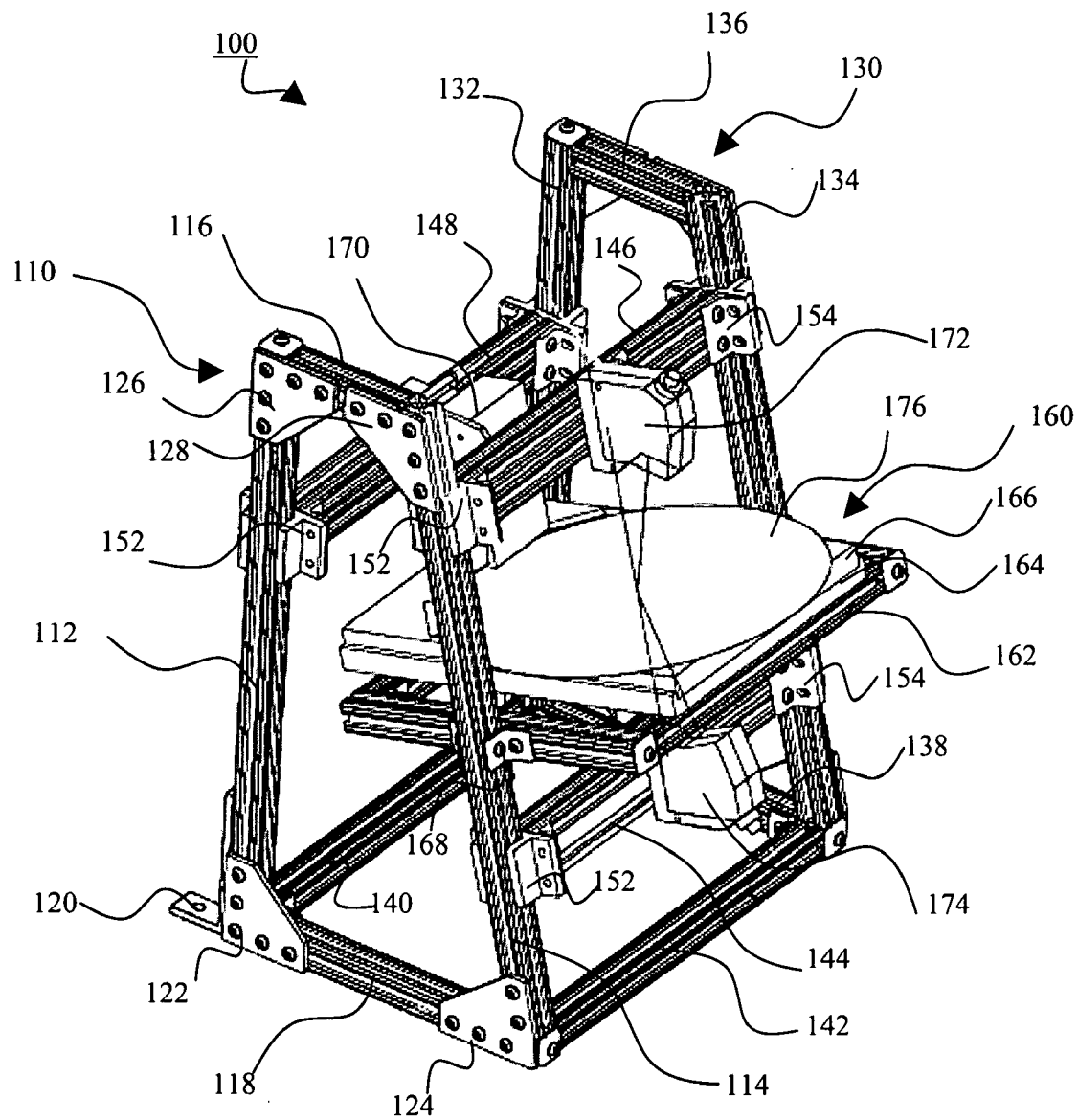
FIG. 1A is an illustration of a perspective view of one embodiment of a wafer inspection apparatus.

Embodiments of the present invention disclose an apparatus and method for improving wafer inspection productivity in a wafer reclaim factory. In various embodiments, an apparatus and method for wafer inspection is described with reference to figures. However, certain embodiments may be practiced without one or more of these specific details, or in combination with other known materials and configurations. In the following description, numerous specific details are set forth, such as specific configurations, dimensions and materials, etc., in order to provide a thorough understanding of the present invention. In other instances, well-known manufacturing techniques have not been described in particular detail in order to not unnecessarily obscure the present invention. Reference throughout this specification to "one embodiment"

means that a particular feature, structure, configuration, or characteristic described in connection with the embodiment is included in at least one embodiment of the invention. Thus, the appearances of the phrase "in one embodiment" in various places throughout this specification are not necessarily referring to the same embodiment of the invention. Furthermore, the particular features, structures, configurations, or characteristics may be combined in any suitable manner in one or more embodiments.

In one aspect, embodiments of the invention improve the efficiency of the wafer reclaim process by improving the incoming and/or outgoing inspection by simultaneously measuring useful wafer characteristics such as wafer ID and thickness, and additionally useful characteristics of deposited films such as refractive index and x-ray fluorescence. In one embodiment, the wafer inspection apparatus is comprised of several wafer measuring components including a wafer ID reader, wafer thickness monitors, refractive index sensor, and/or x-ray fluorescence (XRF) analyzer. In one embodiment, the wafer ID and wafer thickness of incoming wafers are simultaneously measured, so that wafers that are too thin for reclaiming can be sorted out at an early stage. The simultaneous measurement allows a wafer reclaim vendor to save time and expense by that would otherwise be expended if the wafer ID and thickness were measured sequentially. In another embodiment a wafer reclaim vendor is similarly able to save time and expense by simultaneously measuring the refractive index and x-ray fluorescence of films deposited incoming wafers. By doing so the wafers may be sorted according to chemical composition of the films deposited thereon prior to the stripping process, and the stripping process may be specially tailored to wafer composition, thus minimizing the need for re-working wafers which do not strip well in the first instance.

In another aspect, embodiments of the invention provide a user friendly apparatus designed for allowing quick and accurate measuring and sorting of wafers. In one embodiment, the wafer staging area is sloped at an acute angle to horizontal in order to allow easier handling of the wafer by an operator or automated wafer handling system than if the wafer were laying flat on a horizontal surface. In another embodiment, the wafer staging area includes a pin and two laterally opposite restraints for aligning the wafer. In another embodiment the wafer ID reader, thickness monitors, refractive index sensor, and/or XRF analyzer can be connected to a foot-switch for triggering the measurements, thereby allowing an operator's hands to be free to perform other tasks. The connection can be through a cable system, or alternatively be a wireless system such as a Bluetooth connection.

The wafer inspection apparatus may be fabricated with commercially available framing materials. In a preferred embodiment, aluminum 1010 (1 inch×1 inch) t-slot framing is used to build and connect the side frames, traverse frame members, and wafer staging area. T-slot framing is preferred because no welding is required and the framing system can be easily reconfigured by loosening the connectors.

FIG. 1A is an illustration of one embodiment of a wafer inspection apparatus 100. Wafer inspection apparatus 100 includes a pair of side frames 110 and 130. In one embodiment, side frame 110 is the left side frame of apparatus 100, and side frame 130 is the right side frame of apparatus 100. Side frame 110 may include a rear leg 112, a front leg 114, a top connector 116, and a base connector 118. As shown in FIG. 1A, base connector 118 may connect a lower portion of rear leg 112 to a lower portion of front leg 114. In one embodiment, base connector 118 may be flush with a supporting surface (not shown) such as a desktop or floor. Top connector 116 may connect an upper portion of rear leg 112 to an upper portion of front leg 114.

As shown in FIG. 1A, for embodiments employing a 1010 t-slot framing system, the portions of the 1010 t-slot side frame 110 members may be connected to each other using angle joining plates 122, 124, 126, and 128 with 1010 screws and t-nuts or fasteners. In one embodiment, side frame 110 is fastened to a supporting surface (not shown) such as a desktop or floor utilizing a corner bracket 120.

Side frame 130 may include a rear leg 132, a front leg 134, a top connector 136, and a base connector 138. As shown in FIG. 1A, base connector 138 may connect a lower portion of rear leg 132 to a lower portion of front leg 134. In one embodiment, base connector 138 may be flush with a supporting surface (not shown) such as a desktop or floor. Top connector 136 may connect an upper portion of rear leg 132 to an upper portion of front leg 134. Side frame 130 members, may similarly be connected to each other using angle joining plates with 1010 screws and t-nuts or fasteners (not shown). While not shown for clarity, side frame 130 may additionally be fastened to a supporting surface similarly as side frame 110.

Side frames 110 and 130 may be held substantially parallel by one or more traverse frame members 140, 142, 144, 146, and 148. In one embodiment traverse frame members 140 and 142 may be flush with a supporting surface (not shown) such as a desktop or floor. In an embodiment, traverse frame members 140 and 142 may be connected to side frames 110 and 130 using corner brackets and 1010 screws.

In an embodiment, one or more traverse frame members 144, 146, and 148 may be used to additionally support measurement equipment such as, but not limited to, wafer thickness monitors 172 and 174 or wafer ID reader 170. In such an embodiment, it may be preferable to connect the traverse frame members to the side frames 110 and 130 so that they are rigidly attached, yet are adjustable by sliding inline with side frames 110 and 130. In one embodiment, traverse frame members 144, 146, and 148 are attached to side frames 110 and 130 using a combination of double flanged bearings 152 and corner brackets 154. For example, in such an embodiment, the ends of traverse frame members 144, 146, and 148 can be connected to the back ends of double flanged bearings 152 using corner brackets 154. The double flanged bearings 152 in turn can be attached to side frames 110 and 130.

In one embodiment, the double flanged bearings 152 contain Nylon as the bearing surface and can be adjusted for snug or loose fit. When snug, the double flanged bearings 152 are rigidly attached and fixed to the side frames 110 and 130. When loose, the double flanged bearings 152 and traverse frame members 144, 146, and 148 can slide inline with the side frames 110 and 130 using the t-slot frame as a rail.

As shown in FIG. 1A, traverse frame members 144 and 146 may be attached to front legs 114 and 134. When double flanged bearings 152 are used, traverse frame members 144 and 146 may be rigidly attached and additionally be loosened so they may slide inline with the front legs 114 and 134 in order to adjust the distance between traverse frame members 144 and 146. Likewise, traverse frame member 148 may be attached to rear legs 112 and 132 using double flanged bearings 152 such that traverse frame member 148 may be rigidly attached and additionally be loosened so that it may slide inline with rear legs 112 and 132 in order to adjust the position of traverse frame member 148. Such a configuration has several benefits when measurement equipment such as a wafer ID reader 170 and wafer thickness monitors 174 and 172 are attached to the traverse frame members 148, 144, and 146, respectively, as will be discussed in more detail below.

Wafer inspection apparatus 100 additionally includes a wafer staging area 160. The wafer staging area 160 may include a stage 162, support plate 164, and contact plate 166. In one embodiment stage 162, is additionally made of aluminum 1010 t-slot extrusion framing and is rigidly attached to front legs 114 and 134 using corner brackets 168. A support plate 164 is secured to stage 162 in order to provide stability for a contact plate 166, which is secured to the support plate 164. In one embodiment, support plate 164 is a 0.5-0.75 inch thick aluminum plate, and contact plate 164 is a 0.25-0.5 inch thick Teflon plate with a smooth and planar top surface. Contact plate 164 can be any smooth and non-contaminating material so as not to scratch or otherwise damage the wafer surface placed in contact with it. Exemplary materials include but are not limited to PEEK, KELF, and Teflon.

Figure 1B:
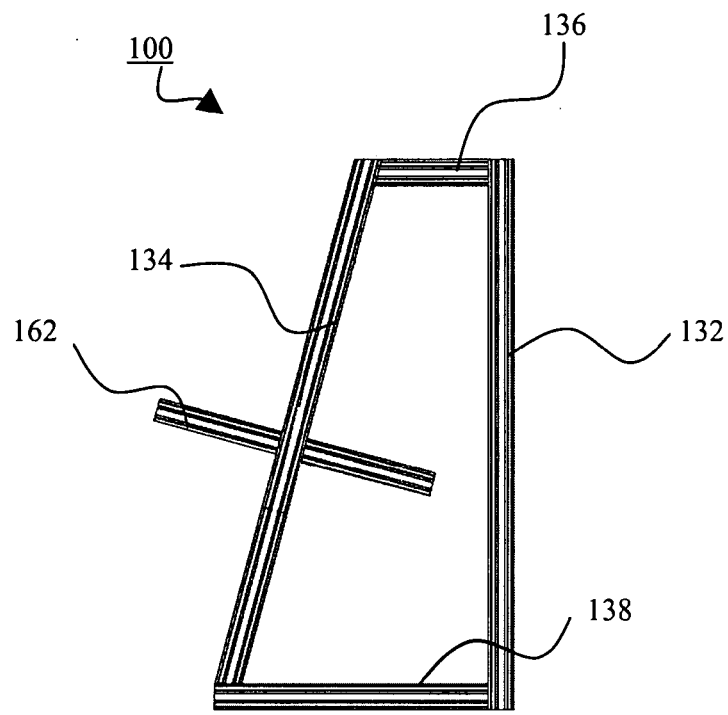
FIG. 1B is an illustration of a side view of the apparatus illustrated in FIG. 1A.

FIG. 1B illustrates a side view from the right side frame 130 of one embodiment of the wafer inspection apparatus 100. As shown in FIG. 1B, rear leg 132 may be connected at a right angle to base connector 138, and stage 162 may be secured to front leg 134 so that stage 162 is sloped at an acute angle to horizontal. Top connector 136 connects rear leg 132 and front leg 134. In one embodiment, the pair of side frames 110 and 130 are parallel and the left side frame 110 is connected similarly as the right side frame 130.

Figure 1C:
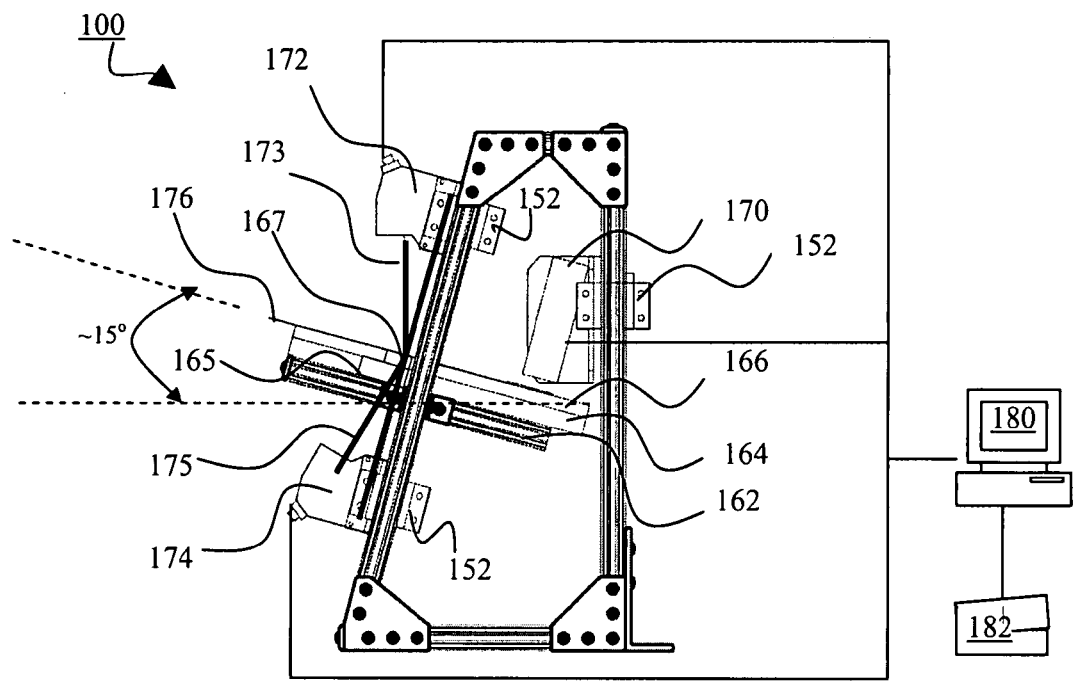
FIG. 1C is an illustration of a side view of the apparatus illustrated in FIG. 1A including a wafer ID reader, upper thickness monitor, and lower thickness monitor connected to a foot-switch.

FIG. 1C illustrates a side view from the right side frame 130 of one embodiment of the wafer inspection apparatus 100 which includes a wafer ID reader 170, an upper thickness monitor 172, and a lower thickness monitor 174. As shown jointly in FIG. 1A and FIG. 1C, wafer ID reader 170 is rigidly secured to traverse frame member 148 located above a portion of contact plate 166. A wafer 176 is placed on the top surface of contact plate 166. In one embodiment, wafer 176 is placed backside (non-device side) facing up, which is the side in which the wafer ID is typically located, and the wafer device-side (deposited film containing side) is facing down. In one embodiment, the top surface of contact plate 166 is sloped at an acute angle to horizontal. In a preferred embodiment, contact plate 166 is sloped at a 15 degree angle to horizontal.

As shown in FIG. 1C, wafer ID reader 170 is preferably secured at a perpendicular angle to contact plate 166, and the corresponding wafer 176 when present. In one embodiment, wafer ID reader 170 is positioned such that when a wafer 176 is placed into an inspection position on contact plate 166 the wafer ID is in the field of view of the wafer ID reader 170. Wafer ID reader 170 may be any commercially available unit, such as the In-Sight 1721 Wafer Reader, available from Cognex Corporation (Natick, Mass.). Preferably wafer ID reader 170 is capable of reading both 2D matrix codes and alphanumeric marks in the same field of view. One advantage of using t-slot framing is that the position of traverse member 148 can be adjusted so that an optimum working distance between the wafer ID reader 170 and wafer 176 can be obtained.

As shown jointly in FIG. 1A and FIG. 1C, upper thickness monitor 172 is rigidly secured to traverse frame member 146 located above a portion of contact plate 166. Additionally, a lower thickness monitor 174 may be rigidly secured to traverse frame member 144 located below a portion of contact plate 166. Thickness monitors 172 and 174 are preferably any commercially available non-contact optics or laser based instruments so that measurements may be taken without damaging or stressing the wafers. Suitable thickness monitors are available from Keyence Corporation (Osaka, Japan). For example the Keyence LT Series Laser Displacement Sensor (confocal measurement methods) may be particularly useful for wafers that have a specular, mirror finish, while the Keyence LK Series Laser Displacement Sensor (triangulation measurement methods) may be particularly useful for wafers that do not have a specular, mirror finish. Confocal and triangulation measurement methods are well known in the art and therefore are not discussed in further detail in order to not obscure the present invention.

Incoming wafers to a reclaim factory have typically been through a number of undisclosed processes. Because of this, some wafers may have some deposited films that cause a warp or bow of the wafers. The warp and bow of an incoming wafer can be in the range of approximately 50-100 microns, and so the wafer thickness may be inaccurate by such amounts if measured using only a single thickness monitor 172 located above a portion of contact plate 166. Therefore, in one embodiment, a sandwich method, as illustrated in FIG. 1A and FIG. 1C, is preferred in order to eliminate the effect of varying warp and bow of incoming wafers. As illustrated in FIG. 1A and FIG. 1C, upper thickness monitor 172 is rigidly secured to traverse frame member 146 located above a portion of contact plate 166, and lower thickness monitor 174 is rigidly secured to traverse frame member 144 located below a portion of contact plate 166. In such a sandwich method, the wafer thickness is essentially measured at a point on the wafer 176 surfaces, and the warp and bow of the wafer 176 becomes irrelevant and does not produce a false result. One advantage of using t-slot framing is that the positions of traverse members 144 and 146 can be adjusted so that an optimum working distance between the wafer thickness monitors 174 and 172, and wafer 176 can be obtained.

In embodiments utilizing a lower thickness monitor 174, it is necessary that the optical beams 175 of the lower thickness monitor 174 are allowed to travel to the bottom surface of wafer 176 unimpeded by staging area 160. FIG. 1C illustrates an embodiment where the upper and lower thickness monitors 172 and 174 are configured for a sandwiching reflective type triangulation method. Optical beams 173 travel unimpeded to the top surface of wafer 176. Optical beams 175 travel unimpeded through the stage 162, support plate 164, and contact plate 166 to the bottom surface of wafer 176. In one embodiment, as shown in FIG. 1, stage 162 is a rigid frame comprised of t-slot extrusions. The opening in stage 162 for optical beams 175 to travel through is the entire center area inside the t-slot extrusion frame. In an embodiment, support plate 164 and contact plate 166 are configured with overlapping through holes 165 and 167, respectively, as shown in FIG. 1C, though not necessarily to scale. It is to be appreciated that sizes and configurations of the openings can vary significantly, while still overlapping to create an unimpeded path for optical beams 175.

Figure 1D:
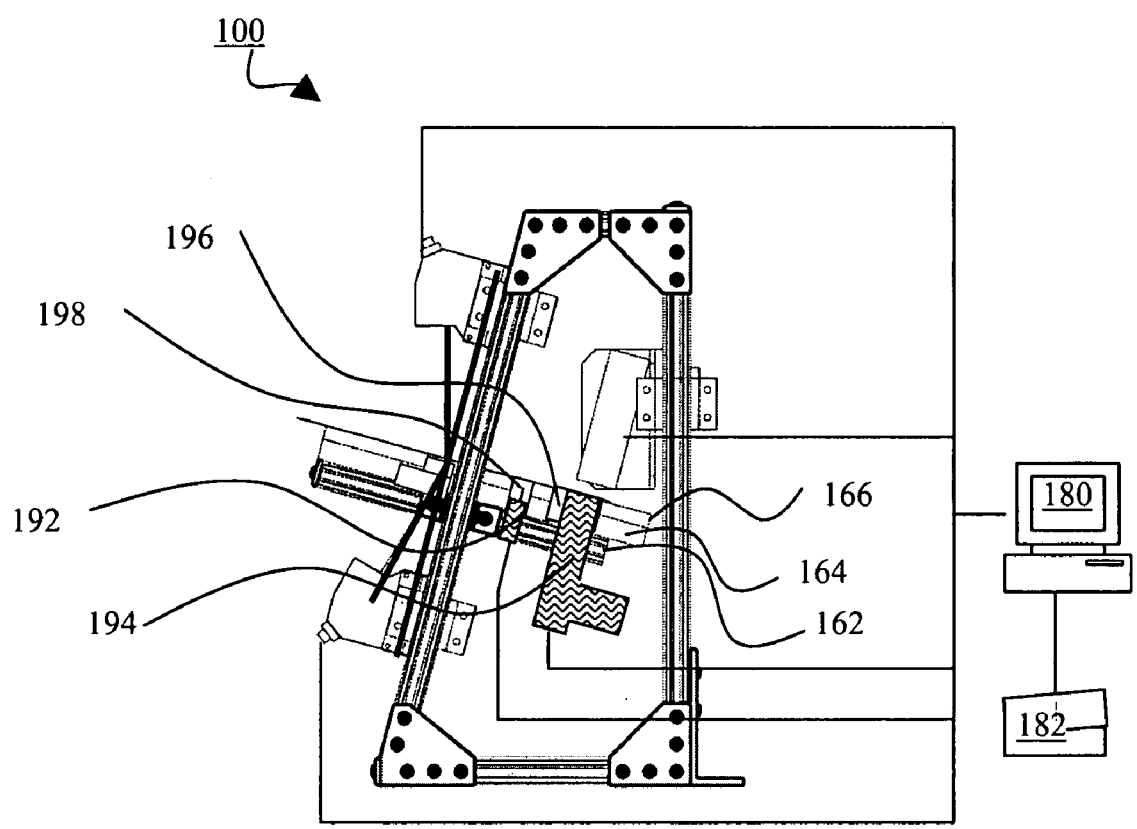
FIG. 1D is an illustration of a side view of the apparatus illustrated in FIG. 1C additionally including an XRF analyzer and refractive index sensor connected to a foot-switch.

FIG. 1D illustrates a side view from the right side frame 130 of one embodiment of the wafer inspection apparatus 100 which includes a refractive index sensor 192 and XRF analyzer 194 which may be added individually or additionally to the wafer ID reader 170, upper thickness monitor 172, and lower thickness monitor 174 of FIG. 1C. As shown in FIG. 1D, refractive index sensor 192 and XRF analyzer 194 may be rigidly secured to stage 162. Though refractive index sensor 192 and XRF analyzer 194 could alternatively be secured to another component such as another traverse member or side frame, etc.

XRF analyzer 194 may be any commercially available unit capable of nondestructive testing, such as the Thermo Scientific NITON XL3t portable XRF analyzer, available from NITON Analyzers HQ (Billerica, Mass.). Preferably, XRF analyzer 194 is capable of measuring the detecting the composition of metal and metal alloy layers contained within the surface layers of a wafer a matter of seconds.

As shown in FIG. 1D, XRF Analyzer 194 may be rigidly secured to stage 162 so that the measurement face is positioned within through hole 196 protruding through both support plate 164 and contact plate 166. Alternatively, through hole 196 can be a pair of separate and overlapping through holes in each support plate 164 and contact plate 166. In a preferred embodiment, the measurement face of XRF analyzer 194 is positioned as close as possible to the bottom surface of wafer 176 without touching wafer 176. In one embodiment, the bottom surface of wafer 176 is the device-side surface. In one embodiment, the distance separate the measurement face of XRF analyzer 194 and the wafer 176 is less than approximately 0.1 mm.

Refractive index sensor 192 may be any commercially available unit capable of nondestructive testing, such as the FISO FRI-Fiber optic refractive index sensor, available from FISO Technologies Inc. (Quebec, Canada). As shown in FIG. 1D, refractive index sensor 192 may be rigidly secured to stage 162 so that the measurement tip is positioned within through hole 198 protruding through both support plate 164 and contact plate 166. Alternatively, through hole 198 can be a pair of separate and overlapping through holes in each support plate 164 and contact plate 166. In one embodiment, the distance separating the measurement tip of refractive index sensor 192 and the bottom surface of wafer 176 is less than 0.1 mm, though the distance can be can be more or less.

Figure 2:
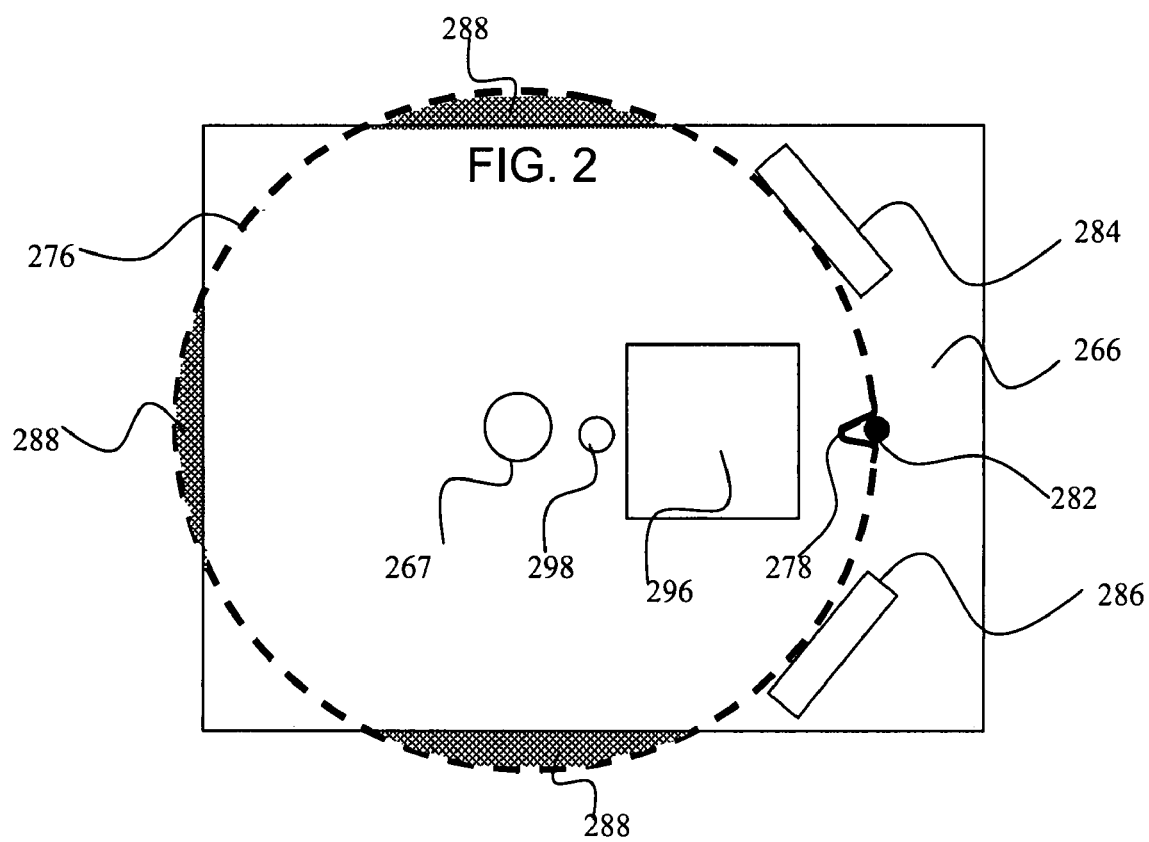
FIG. 2 is an illustration of a top view of a contact plate configured for a 300 mm wafer.

FIG. 2 provides a detailed illustration of a contact plate 266 configured for a 300 mm wafer, though the illustration is only meant to be exemplary, and it should be appreciated that the apparatus could be configured for other sized substrates as well. As shown in FIG. 2, contact plate 266 includes a pair of laterally opposite restraints 284 and 286 and a pin 282 extending from a top surface of contact plate 266. Contact plate 266 may additionally include a through hole 267 for when the apparatus is used in a sandwiching method. In one embodiment, through hole 267 is approximately 1.0 inch in diameter. Contact plate 266 may additionally include a through hole 296 approximately 3×3 inches for XRF analyzer 194, and through hole 298 approximately 0.4 inch in diameter for refractive index sensor 192, to measure films on wafer 276.

FIG. 2 additionally illustrates a 300 mm wafer 276 positioned on the top surface of contact plate 266. As shown, when wafer 276 is positioned in an inspection position, the wafer notch 278 is aligned with pin 282, and wafer 276 is additionally propped against restraints 284 and 286 so that wafer 276 is secure in the x-y orientation parallel to the top surface of contact plate 266. In one embodiment, pin 282 is approximately 0.110 inches in diameter. In one embodiment, pin 282 and restraints 284 and 286 are made of a material such as but not limited to PEEK, KELF, and Teflon.

One advantage of the configuration illustrated in FIG. 2 is that three areas 288 of wafer 276 hang over the edges of contact plate 266. An operator or automated wafer handling system may handle the edges of areas 288 in order to place the wafer 276 onto contact plate 266, align the wafer 276 in an x-y orientation parallel to the surface of contact plate 266, and remove wafer 276 from contact plate 266.

When wafers enter a reclaim factory, they often must be processed and returned to customers within days. As described above, embodiments of the invention describe an apparatus that improves the efficiency of the wafer reclaim process by providing for simultaneous wafer ID and wafer thickness measurements. In addition, other measurement equipment may be attached to the apparatus that assists in the wafer reclaim process such as a refractive index sensor and XRF analyzer. In another aspect, embodiments of the invention describe an apparatus designed for quick and accurate measuring of the wafers, which may be performed manually by the user or by an automated wafer handling system which transfers wafers to and from the stage.

Referring to FIG. 1, apparatus 100 is designed so that in one embodiment an operator may stand in front of front legs 114 and 134. The operator may manually take a notched wafer 176 and place the wafer onto the top sloped surface of contact plate 166 such that the notch is facing down the slope. As shown in FIG. 1A, the top surface of contact plate 166 may be sloped downward, with the front surface (front leg side 114, 134) being higher than back surface (rear leg side 112, 132). Referring to FIG. 2, the operator may then align the notched wafer 276 in the x-y direction parallel to the top sloped surface of the contact plate 266 by aligning the notch 278 with pin 282 located on the top surface of contact plate 266, and by propping the wafer 276 against a pair of laterally opposite restraints 284 and 286 that are located on opposite sides of pin 282. One advantage of the configuration in FIG. 2 is that the operator may handle the edges of areas 288 in order to assist in positioning the wafer 276. Another advantage is that the contact plate is secured at an acute angle to horizontal, which makes it easier for the natural arm movement of an operator standing in front of the apparatus to place wafers onto and remove wafers from contact plate 266. Because the surface of contact plate 266 is sloping downward towards pin 282 and restraints 284 and 286, the wafer 276 is held in place by gravity.

In one embodiment, the operator may then simultaneously measure the wafer ID and wafer thickness. As shown in FIG. 1C, the wafer ID reader 170 and thickness monitors 172 and 174 can all be connected to a computer 180 and foot-switch 182. The computer 180 may for example be a local computer or a host computer connected through the factory manufacturing enhancement system (MES) which is a database for the entire factory automation. The operator may trigger simultaneous measuring of the wafer ID and wafer thickness by triggering a foot-switch 182. One advantage of the foot-switch 182 is that this allows the operator's hands to remain free for handling wafers and performing other functions.

In one embodiment, the wafer ID reader 170 reads both an alphanumeric mark as well as a 2D code on the wafer 176. In other embodiments, wafer ID reader 170 may only measure one or the other, or may measure other markings such as a bar code.

In one embodiment, the wafer thickness is measured using only a single thickness monitor. In other embodiments, the wafer thickness is measured using a sandwiching method utilizing an upper optics-based thickness monitor 172 and a lower optics-based thickness monitor 174. Wafer thickness may be measured using a reflective type triangulation method, which is preferable for wafers with non-specular surfaces, or a reflective type confocal method, which is preferable for wafers with specular surfaces, though additional non-contact thickness measurement techniques may also be used.

In another embodiment, the operator may additionally measure the refractive index and x-ray fluorescence of at least one film disposed on the wafer device side facing down, simultaneously with measuring the wafer ID and wafer thickness. Similar to the wafer ID reader 170 and thickness monitors 172 and 174, the refractive index sensor 192 and XRF Analyzer 194 can be connected to a computer 180 and foot-switch 182.

After the operator has measured the wafer ID and thickness, and/or film refractive index and x-ray fluorescence, the operator may manually remove wafer 276 from the contact plate 266 by handling the edges of areas 288, shown in FIG. 2. It is to be appreciated that while a method of operation has been described in which an operator manually positions a wafer on the apparatus and performs a measurement, additional embodiments are also within the scope of the invention in which an automated wafer handling system replaces the operator in the wafer handling, positioning, and measurement functions.

Figure 3:
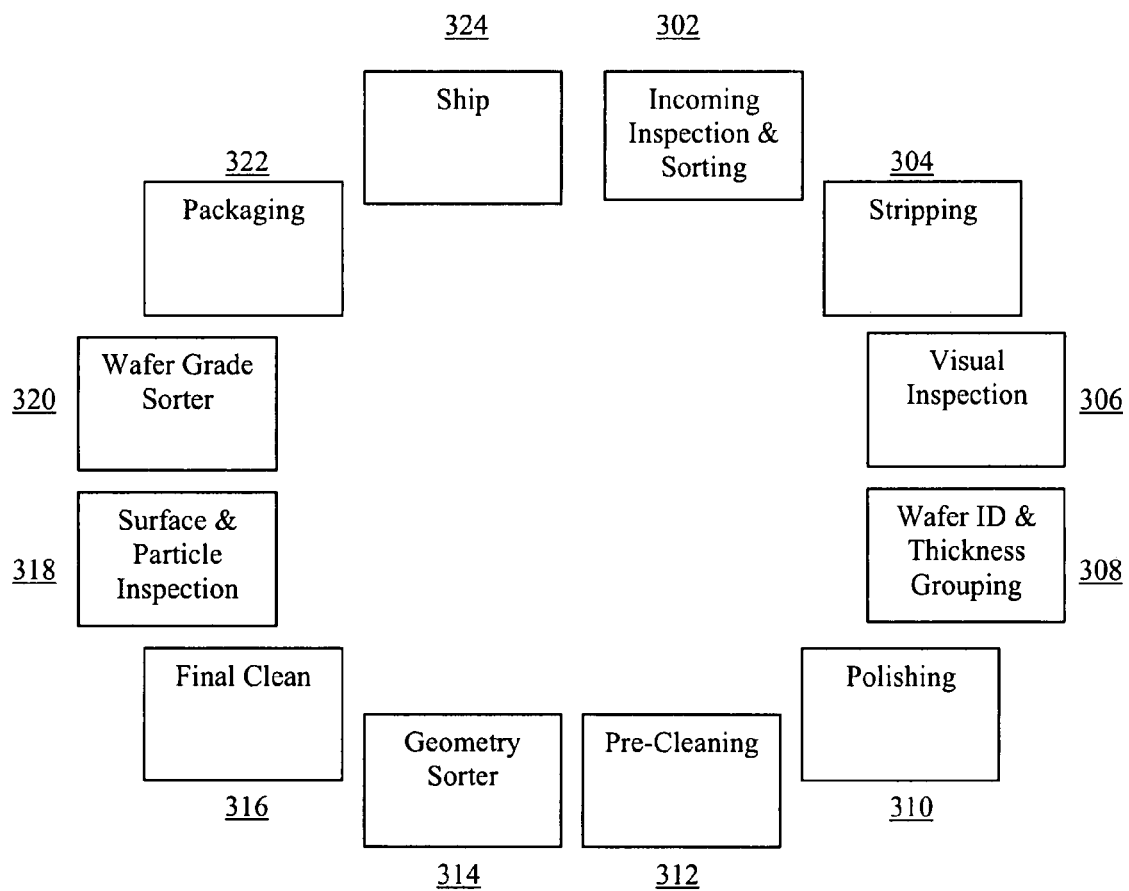
FIG. 3-FIG. 5 are flow diagrams of embodiments utilizing a wafer inspection apparatus in a wafer reclaim process.

FIG. 3 illustrates one embodiment of a wafer reclaim process. Such an embodiment involves several process steps with in-line quality checks using metrology and inspection. At step 302 incoming wafers are visually inspected and sorted. For example, incoming wafers are visually inspected and sorted into separate groups for Cu containing films, Al containing films, and oxide, nitride, and/or poly containing films in order to reduce cross-contamination between reclaimed wafers during processing. Multi-layer patterned wafers, and chipped or broken wafers are additionally sorted out from the reclaim process at step 302. Then at step 304 the wafers are stripped using various processing techniques such as wet strips, wafer grinding, and silicon etches tailored to the specific group (for example, Cu, Al, or oxide/nitride/poly). The wafers are then visually inspected again at step 306 to verify all patterns were removed during the stripping step 304. Then at step 308 the wafer ID and thickness are measured. The reclaim vendor may then correlate wafer ID with wafer thickness and group the wafers by wafer ID (part number) and/or thickness. Typically, for prime 300 mm wafers having an original thickness of 775 µm, customers may wish to only have wafers with a thickness greater than 650 µm, for example, shipped back. Accordingly, the reclaim vendor can group and sort out the wafers than are too thin for reclaiming at this step. The wafers are then polished at step 310. Polishing may be double-side polishing (DSP) or single-side polishing (SSP) depending on customer specifications. The polished wafers are then thoroughly cleaned in steps 312 and 316, inspected for surface quality and impurities at step 318, sorted at 314 and 320, and packaged 322 according to customer specification. The reclaimed wafers are then shipped to the customer at step 324.

Figure 4:
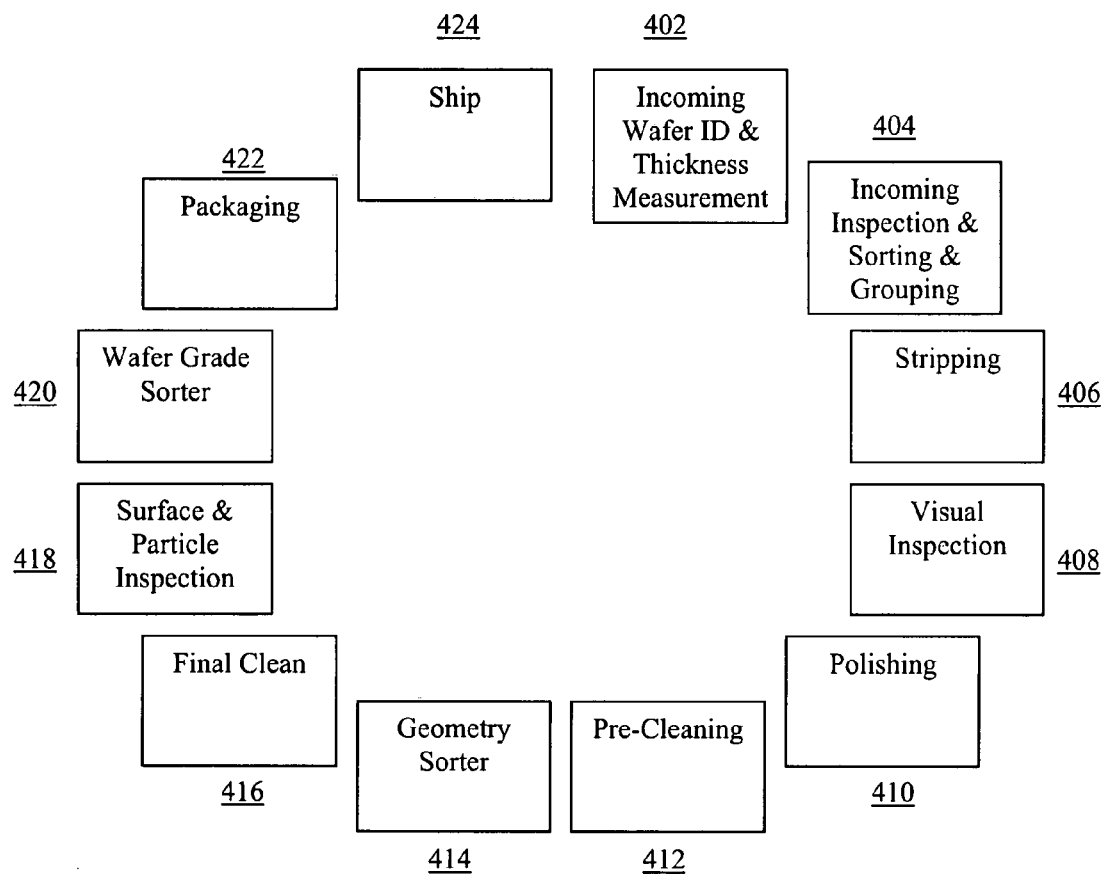

FIG. 4 illustrates an alternative embodiment of a wafer reclaim process in which incoming wafer ID and thickness is measured in the same step. As shown in FIG. 4, incoming wafer ID and thickness are measured at step 402. At step 404 the wafers may then be visually inspected. Wafers may be sorted into separate groups for Cu containing films, Al containing films, and oxide, nitride, and/or poly containing films. Additionally, multi-layer patterned wafers, chipped or broken wafers, and wafers that would be expected to be too thin for reclaiming at the completion of all processing may be sorted out. Thus, by identifying at initial stage 402 the wafers that would be expected to be too thin for reclaiming after completion of all processing, the wafer reclaim vendor can sort out those wafers at step 404 and save time and expense that would otherwise be expended by stripping the non-reclaimable thin wafers. Only the wafers that can be expected to meet the customers' thickness requirements at the completion of all processing are then stripped at step 406, inspected 408, and then thoroughly polished, cleaned, inspected, sorted, packaged, and shipped in steps 410-424 similarly as in steps 310-324.

Figure 5:
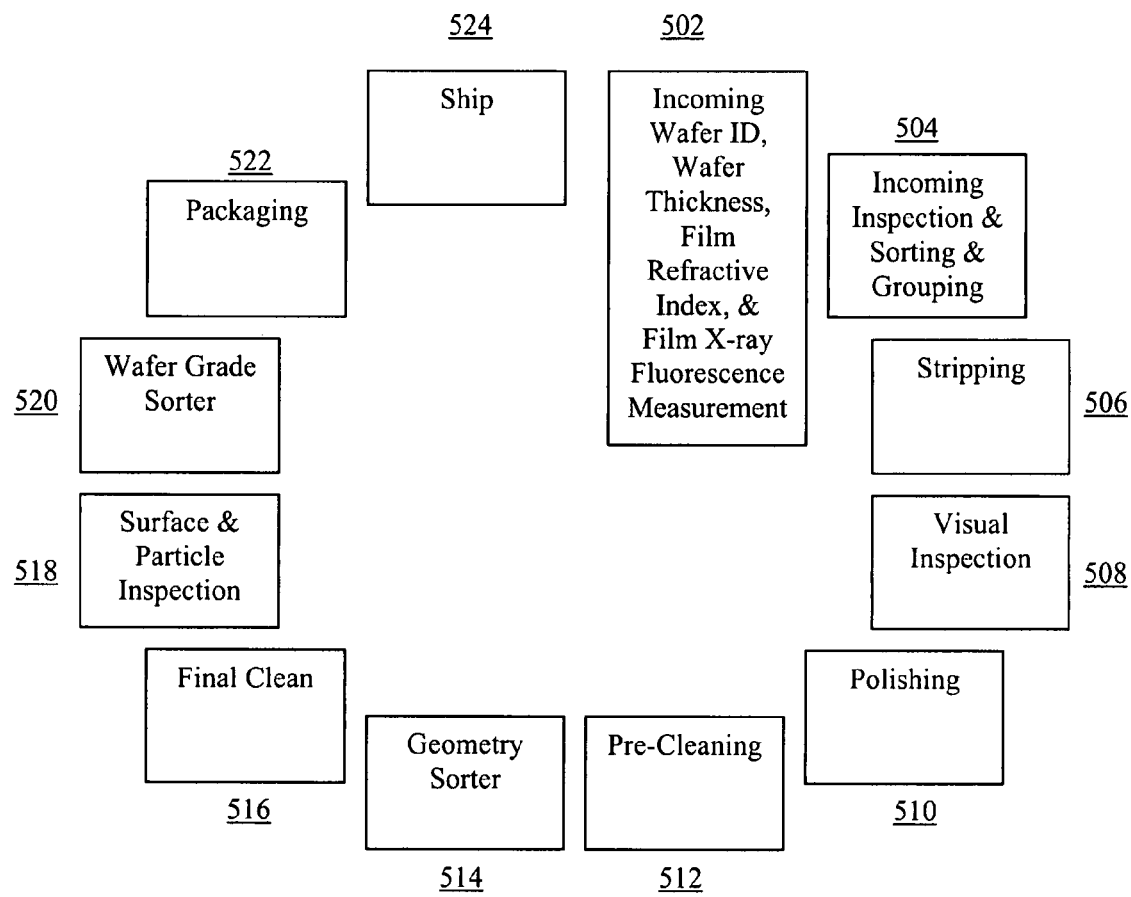

FIG. 5 illustrates an alternative embodiment of a wafer reclaim process in which the refractive index and x-ray fluorescence of at least one film may be measured in the same step in addition to measuring incoming wafer ID and thickness. As shown in FIG. 5, incoming wafer ID and thickness, refractive index, and x-ray fluorescence can be measured and correlated at step 502. Such an embodiment takes advantage of the ability to characterize the film (or films) deposited on the wafer surface at an initial stage. By identifying the refractive index of a deposited film, the wafer reclaim vendor can correlated the measured refractive index with that of a known film composition and further sort the wafers into groups at step 504, something that a reclaim vendor may not be able to do accurately and consistently with a visual inspection only. For example, at step 504 the reclaim vendor may further sort the wafers into separate groups for films such as oxide, nitride, low-k, and even bare wafers, all of which may not be accurately and consistently distinguishable based on a visual inspection only. In addition, the x-ray fluorescence measurement would be able to distinguish between the types of metal films present, and identify those metals present that would be difficult to detect in a visual inspection only. In another embodiment, the vendor could additionally measure, sort, and group other film characteristics such as, but not limited to, film thickness in order to enhance the reclaim process.

Then at step 506, the wafers can be subjected to a specifically tailored stripping process for the specific materials films present or not present. This can avoid problems such as unnecessarily over etching the wafer that occurs when the chemistry of the deposited layers is unknown. Over stripping the wafers in acid baths roughens the surface and requires additional polishing time at step 510. Additionally, knowledge of the film type enables the reclaim vendor to ensure that appropriate stripping processes are applied to the appropriate wafers, thus reducing the likelihood of having to re-work (re-strip) wafers. Thus, by determining the chemistry of the deposited layers at an early stage through methods such as refractive index or x-ray fluorescence can enhance overall reclaim cycle time. After stripping at step 506, the wafers are inspected 508, and then thoroughly polished, cleaned, inspected, sorted, packaged, and shipped in steps 510-524 similarly as in steps 310-324.

It is to be appreciated that while FIG. 3-FIG. 5 provide specific detailed processing sequences utilizing a wafer inspection apparatus in which incoming wafer characteristics are measured in the same step, that the scope of the invention would additionally include other process sequences utilizing the wafer inspection apparatus. It is also to be appreciated that the wafer inspection apparatus could be used for outgoing wafers after stripping, polishing, and cleaning steps have been performed.

Although the present invention has been described in language specific to structural features and/or methodological acts, it is to be understood that the invention defined in the appended claims is not necessarily limited to the specific features or acts described. The specific features and acts disclosed are instead to be understood as particularly graceful implementations of the claimed invention useful for illustrating the present invention.

What is claimed is:

1. A wafer inspection apparatus comprising:
   a main frame comprising a first side frame and a second side frame, wherein the first and second side frames are held substantially parallel by a plurality of traverse frame members;
   a contact plate comprising a pair of laterally opposite restraints and a pin extending from a top surface of the contact plate; wherein the contact plate is secured at an acute angle to horizontal;
   a wafer ID reader rigidly secured to a first traverse frame member located above a portion of the contact plate
   a first optics-based wafer thickness monitor secured to a second traverse frame member located above a portion of the contact plate; and a second optics-based wafer thickness monitor secured to a third traverse frame member located below a portion of the contact plate.

2. The apparatus of claim 1, wherein a top surface of the contact plate is at an angle of approximately 15 degrees to horizontal.

3. The apparatus of claim 1, further comprising a footswitch for activating the read function on the wafer ID reader and the first and second optics based thickness monitors.

4. The apparatus of claim 1, wherein the first and second optics based thickness monitors are configured for a sandwiching measurement method.

5. The apparatus of claim 1, wherein the first and second optics based thickness monitors are configured for a reflective type triangulation measurement method.

6. The apparatus of claim 1, wherein the first and second optics based thickness monitors are configured for a reflective type confocal measurement method.

7. The apparatus of claim 1, further comprising at least one component selected from the group consisting of a refractive index sensor and XRF analyzer.

8. The apparatus of claim 1, wherein the contact plate is comprised of a material selected from the group consisting of Teflon, PEEK, and KELF.

9. A wafer inspection apparatus comprising:
a main frame comprising:
a first side frame comprising a first rear leg, a first front leg, a first top connector, and a first base connector, wherein the first top connector connects an upper portion of the first rear leg to an upper portion of the first front leg, and
the first base connector connects a lower portion of the first rear leg to a lower portion of the first front leg, and
a second side frame comprising a second rear leg, a second front leg, a second top connector, and a second base connector, wherein the second top connector connects an upper portion of the second rear leg to an upper portion of the second front leg, and the second base connector connects a second portion of the second rear leg to a lower portion of the second front leg,
a wafer staging area comprising:
a stage rigidly attached to the first front leg and the second front leg, the stage comprising a first opening,
a support plate secured to the stage, the support plate including a second opening that overlaps the first opening, and
a contact plate secured to the support plate, the contact plate including a third opening that overlaps the first and second openings, the contact plate further comprising a pair of laterally opposite restraints and a pin for aligning the notch of a wafer extending from the top surface of the contact plate;
a wafer ID reader rigidly secured to a first traverse frame member above a portion of the wafer staging area, the first traverse frame member being connected to the first rear leg and the second rear leg;
a first optics-based thickness monitor rigidly secured to a second traverse frame member above a portion of the wafer staging area, the second traverse frame member being connected to the first front leg and the second front leg; and
a second optics-based thickness monitor rigidly secured to a third traverse frame member below a portion of the wafer staging area, the second traverse flame member being connected to the first front leg and the second front leg;
wherein the first side flame and the second side frame are held substantially parallel by the first, second, and third traverse flame members.

10. The apparatus of claim 9, wherein the second optics-based thickness monitor is secured below a portion of the wafer staging area such that the optical beams emitted from the second optics-based thickness monitor travel through the first, second, and third openings.

11. The apparatus of claim 9, wherein the third opening is an approximately 1.0 inch diameter hole.

12. The apparatus of claim 11, wherein the center of the third opening is approximately 5.33 inches from the pin center.

13. The apparatus of claim 9, further comprising a refractive index sensor and XRF analyzer rigidly attached to the wafer staging area.

14. A wafer inspection apparatus comprising:
a main frame;
a contact plate coupled with the main frame; a wafer ID reader secured to the main frame above a portion of the contact plate;
a first optics-based wafer thickness monitor secured to the main frame above a portion of the contact plate; and
a second optics-based wafer thickness monitor secured to the main frame below a portion of the contact plate.

15. The apparatus of claim 14, further comprising at least one component selected from the group consisting of a refractive index sensor and XRF analyzer secured to the main frame.

16. The apparatus of claim 14, wherein the contact plate is comprised of a material selected from the group consisting of Teflon, PEEK, and KELF.

17. The apparatus of claim 14, wherein the contact plate comprises a pair of laterally opposite restraints and a pin extending from a top surface of the contact plate.

* * * * *